United States Patent [19]

Petzoldt et al.

[11] Patent Number: 5,093,250
[45] Date of Patent: Mar. 3, 1992

[54] PROCESS FOR PRODUCING OPTICALLY ACTIVE BICYCLO[3.3.0]OCTANEDIONE CARBOXYLIC ACID ESTERS

[75] Inventors: Karl Petzoldt; Werner Skuballa, both of Berlin, Fed. Rep. of Germany

[73] Assignee: Schering Aktiengesellschaft, Berlin & Bergkamen, Fed. Rep. of Germany

[21] Appl. No.: 237,113

[22] PCT Filed: Nov. 12, 1987

[86] PCT No.: PCT/DE87/00518

§ 371 Date: Jul. 13, 1988

§ 102(e) Date: Jul. 13, 1988

[87] PCT Pub. No.: WO88/03569

PCT Pub. Date: May 19, 1988

[30] Foreign Application Priority Data

Nov. 13, 1986 [DE] Fed. Rep. of Germany ....... 3638760

[51] Int. Cl.$^5$ .......................... C12P 7/62; C12P 7/38; C12P 7/24; C12N 9/76
[52] U.S. Cl. .................................... 435/135; 435/147; 435/149; 435/213; 435/280
[58] Field of Search ............... 435/135, 147, 148, 149, 435/195, 196, 213, 180, 280

[56] References Cited

U.S. PATENT DOCUMENTS 4,800,162  1/1989  Matson ................................. 435/148

FOREIGN PATENT DOCUMENTS

J47495  3/1983  Japan ................................. 435/149
2178423  2/1987  United Kingdom .

Primary Examiner—Douglas W. Robinson
Assistant Examiner—Irene Marx
Attorney, Agent, or Firm—Millen, White and Zelano

[57] ABSTRACT

Claimed is a process for the production of optically active bicyclo[3.3.0]octanedione-carboxylic acid esters of Formula I

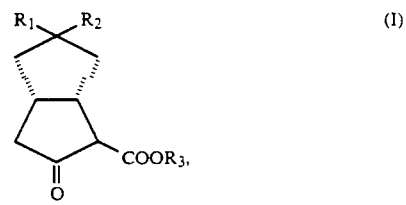

wherein
$R_1$ and $R_2$ jointly represent an oxygen atom, or
$R_1$ and $R_2$ individually represent the residue $OR_4$ where $R_4$ means methyl- or ethyl-, and
$R_3$ is a straight or branched-chain alkyl group of 1–3 carbon atoms, comprising enantioselectively saponifying and decarboxylating with α-chymotrypsin an optically inactive, prochiral bicyclo[3.3.0]octanedionedicarboxylic acid diester of Formula II

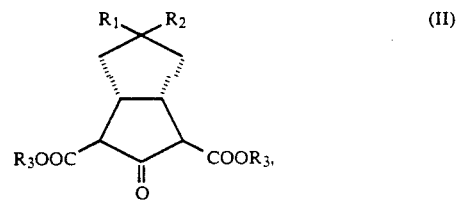

wherein $R_1$, $R_2$ and $R_3$ have the meanings set forth above, and recovering a compound of Formula I.

1 Claim, No Drawings

PROCESS FOR PRODUCING OPTICALLY ACTIVE BICYCLO[3.3.0]OCTANEDIONE CARBOXYLIC ACID ESTERS

BACKGROUND OF THE INVENTION

Optically active 6a-carbaprostacyclin and, in particular, several compounds derived therefrom possess, as stable analogs of the natural prostacyclin [PGI$_2$], a high therapeutic utility [R. C. Nickolson, M. H. Town, H. Vorbrüggen: "Prostacyclin-Analogs", Medicinal Research Reviews, 5, 1:1-53 (1985)]. The syntheses listed in this more recent overview are long and lead, in part, merely to racemic carbacyclins. The syntheses resulting in carbacyclins in the absolute configuration corresponding to natural PGI$_2$ are especially expensive. This is due to the fact that readily accessible, suitable starting materials are achiral, and the optical activity must be introduced during the course of the synthesis into intermediate stages suitable for this purpose.

Several syntheses start with already optically active 7α-hydroxy-6β-hydroxymethyl-2-oxabicyclo[3.3.0]-octan-3-one derivatives. Although this solves the problem of introducing optical activity, it is necessary to perform still further multistage synthesis sequences for the substitution of the 2-oxa function by a methylene group in order to obtain derivatives of 3α-hydroxy-2β-hydroxymethylbicyclo[3.3.0]octan-7-one which are the ones suitable for the addition of the α- and ω-chains in each case typical for the carbacyclin analogs.

A more recent publication describes the use of cis-bicyclo[3.3.0]octane-3,7-dione derivatives for the synthesis of optically active carbacyclins. Kojima et al. describe a process in Chem. Pharm. Bull. 33:2688 (1985) which includes the separation of diastereomeric salts of racemic 7,7-ethylenedioxy-3α-hydroxy-cis-bicyclo[3.3.0]octane-2-carboxylic acid.

This method still requires seven reaction steps in order to obtain the starting material for carbacyclin analogs, starting with 3-oxoglutaric esters. Additionally, the procedure passes through an unstable β-keto acid intermediate stage.

Furthermore, no synthesis route permitting simple production is known for the preparation of optically active carbacyclin analogs as described above.

SUMMARY OF THE INVENTION

It has now been found that the above-mentioned prochiral dicarboxylic acid esters of prostacyclin and carbacyclin intermediate stages can be saponified and decarboxylated enantioselectively to the monocarboxylic acid esters in very good yields by using enzymes, particularly α-chymotrypsin.

The invention is particularly suited for the enzymatic enantioselective monosaponification and decarboxylation of the prostacyclin and carbacyclin intermediates 1-4 set forth below.

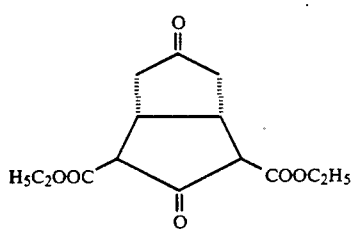

1

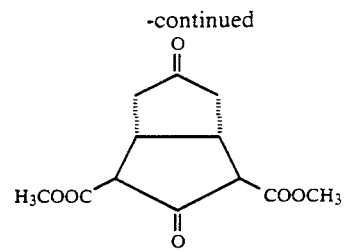

2

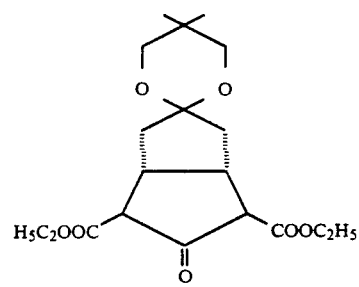

3

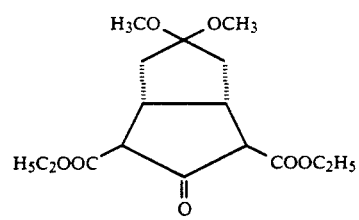

4

Accordingly, the invention relates to a process for producing optically active bicyclo[3.3.0]octane-dionecarboxylic acid esters of Formula I

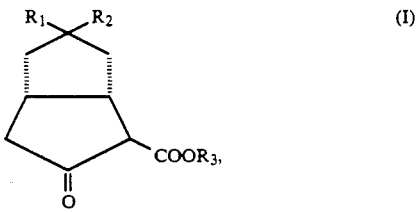

(I)

wherein
R$_1$ and R$_2$ jointly represent an oxygen atom or the residue —O—X—O— where X means a straight or branched-chain alkylene group of 1-7 carbon atoms, or R$_1$ and R$_2$ individually represent the residue OR$_4$ where R$_4$ means a straight or branched-chain alkyl of 1-7 carbon atoms, and R$_3$ is a straight or branched-chain alkyl group of 1-10 carbon atoms, characterized in that a prochiral bicyclo[3.3.0]octanedione dicarboxylic acid diester of Formula II

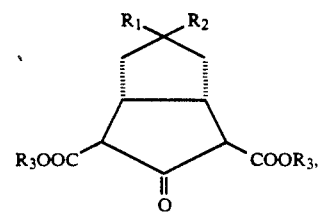

(II)

wherein $R_1$, $R_2$ and $R_3$ have the meanings set forth above, is enantioselectively saponified and decarboxylated with enzymes.

If X means a straight-chain or branched-chain alkylene residue of 1-7 carbon atoms, the following residues are meant:

—$(CH_2)_n$— wherein $n=1-7$ (methylene, ethylene, tri-, tetra-, penta-, hexa- and heptamethylene),
—$C(CH_3)_2$—, —$CH(CH_3)$—, —$CH(CH_3)$—$CH_2$—, —$C(CH_3)_2$—$CH_2$—, —$CH_2$—$CH(CH_3)$—, $CH_2$—$C(CH_3)_2$, —$CH_2$—$CH(CH_3)$—$CH_2$—, —$CH_2$—$C(CH_3)_2$—$CH_2$—, —$CH$—$(C_2H_5)$—, —$C(C_2H_5)_2$—, —$CH(C_2H_5)$—$CH_2$—, —$C(C_2H_5)_2$—$CH_2$—, —$CH_2$—$CH(C_2H_5)$—, —$CH_2$—$C(C_2H_5)_2$—, —$CH_2$—$CH(C_2H_5)$—$CH_2$—, —$CH_2$—$C(C_2H_5)_2$—$CH_2$— etc.

$R_3$ and $R_4$ as straight-chain or branched-chain alkyl residues of 1-10 and, respectively, 1-7 carbon atoms mean methyl, ethyl, n-propyl, isopropyl, n-butyl, isobutyl, sec-butyl, tert-butyl, n-pentyl, isopentyl, sec-pentyl, neopentyl, n-hexyl, isohexyl, n-heptyl, isoheptyl, octyl, nonyl, decyl.

The enzymes utilized in accordance with this invention can be employed in dissolved or suspended form as well as immobilized, e.g. on BrCN-activated "Sepharose" or on oxirane-acrylic beads.

The starting compounds for the above process are known or can be prepared as follows:

REFERENCE EXAMPLE 1

2,4-Bisethoxycarbonylbicyclo[3.3.0]octane-3,7-dione

At 25° C., a solution of 86 g of acetone-dicarboxylic acid diethyl ester and 59 g of acetoxycyclopentenone in 170 ml of ethanol is added to a suspension of 82 g of potassium carbonate in 680 ml of ethanol, and the mixture is stirred for 24 hours at 25° C., then concentrated under vacuum, combined with water, and acidified with 20% citric acid solution to pH 4. The mixture is extracted three times with methylene chloride, the organic phase is washed three times with brine, dried over sodium sulfate, and evaporated under vacuum. The residue is purified by chromatography on silica gel. With ethyl acetate/hexane, 70 g of the title compound is eluted as a colorless oil.

IR ($CHCl_3$) 3020, 2960, 1740, 1665, 1623, 1445 cm$^-$

REFERENCE EXAMPLE 2

2,4-(Bismethoxycarbonyl)bicyclo[3.3.0]octane-3,7-dione

A mixture of 60 g of acetoxycyclopentenone and 120 ml of acetonedicarboxylic acid dimethyl ester is added dropwise at about 20° C. to a mixture of 240 ml of acetone-dicarboxylic acid dimethyl ester and 120 g of diisopropylethylamine. The mixture is then stirred for 20 hours at room temperature, acidified with 20% citric acid to pH 3-4, and extracted three times with respectively 300 ml of methylene chloride. The organic phase is washed with 100 ml of 5% sodium bicarbonate solution and with brine, dried over sodium sulfate, and evaporated under vacuum. The excess acetonedicarboxylic acid dimethyl ester is removed by distillation at 0.07 mbar and 97° C. and the distillation residue is purified by column chromatography on silica gel. With ethyl acetate/hexane (3+2), 39 g of the title compound is eluted as a colorless oil.

IR ($CHCl_3$) 3022, 2961, 1740, 1665, 1624, 1445 cm$^{-1}$

REFERENCE EXAMPLE 3

2,4-Bisethoxycarbonyl-7,7-(2,2-dimethylpropylene-1,3-dioxy)bicyclo[3.3.0]octan-3-one At 25° C., 83 mg of p-toluenesulfonic acid, 8.2 g of 2,2-dimethylpropane-1,3-diol and 4.3 g of triethyl orthoformate are added to a solution of 10 g of 2,4-bisethoxycarbonylbicyclo[3.3.0]octane-3,7-dione (preparation: Reference Example 1) in 165 ml of methylene chloride. The mixture is stirred for 24 hours at 25° C., combined with 500 ml of methylene chloride, and washed once with 30 ml of 5% strength sodium bicarbonate solution and three times with brine. The mixture is dried over sodium sulfate and evaporated under vacuum. The residue is purified by chromatography on silica gel. With ethyl acetate/hexane (3+2), 10.3 g of the title compound is eluted as a colorless oil.

IR ($CHCl_3$): 2955, 2883, 1735, 1665 cm$^{-1}$

REFERENCE EXAMPLE 4

2,4-Bisethoxycarbonyl-7,7-dimethoxybicyclo[3.3.0]octan-3-one

At 25° C., 330 mg of p-toluenesulfonic acid and 1.6 ml of trimethyl orthoformate are added to a solution of 9.6 g of 2,4-bisethoxycarbonylbicyclo[3.3.0]octane-3,7-dione (preparation: Reference Example 1) in 330 ml of methanol. The mixture is stirred for 3 hours at 25° C., combined with 80 ml of 5% strength sodium bicarbonate solution, extracted three times with respectively 300 ml of methylene chloride, dried over sodium sulfate, and evaporated under vacuum. The residue is purified by chromatography on silica gel. With ethyl acetate/hexane (1+1), 7 g of the title compound is obtained as a colorless oil.

The compounds of Formula I prepared according to the process of this invention serve for the production of pharmacologically effective prostacyclin derivatives.

The compounds of general Formula I can be utilized for the preparation of pharmacologically effective carbacyclin derivatives [see, in this connection, R. C. Nickolson, M. N. Town and H. Vorbrüggen, "Medicinal Research Review" 5:1 (1985) and P. A. Aristoff in "Advances in Prostaglandin, Thromboxane and Leukotriene Research" 15 (1985)].

Starting with (1S,2R,5R)-2-ethoxycarbonyl-7,7-(2,2-dimethylpropylene-1,3-dioxy)bicyclo[3.3.0]-octan-3-one, the active agent iloprost is obtained, for example, in a multistage synthesis.

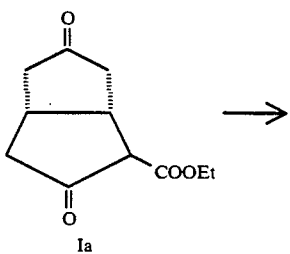

Ia

-continued
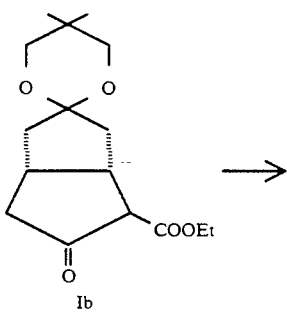
Ib
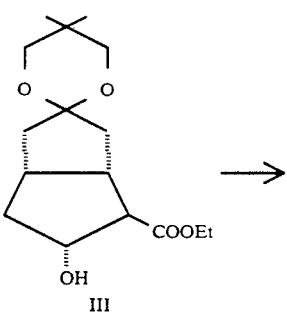
III
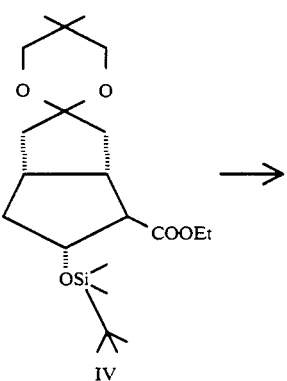
IV
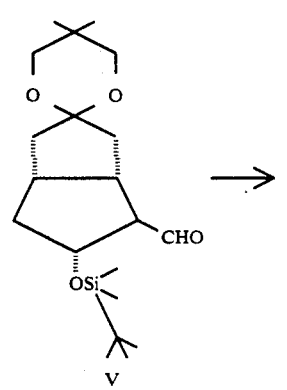
V
-continued
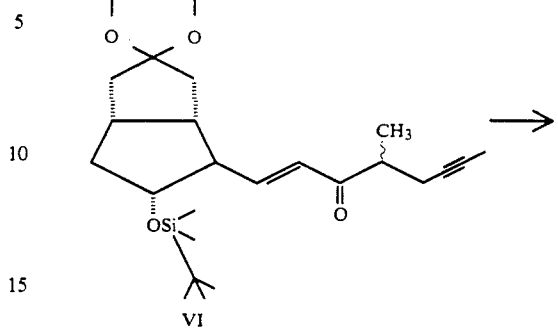
VI
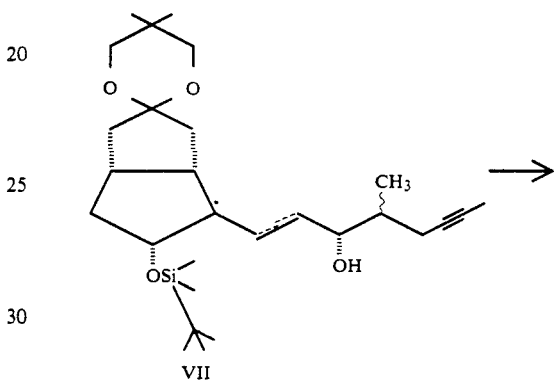
VII
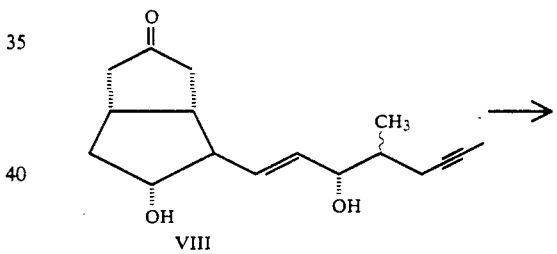
VIII
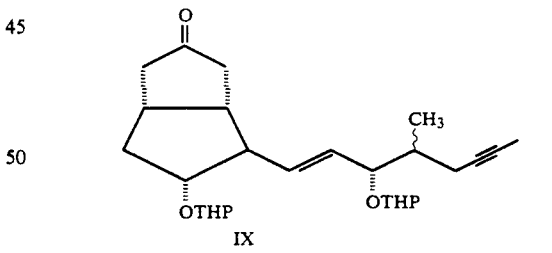
IX
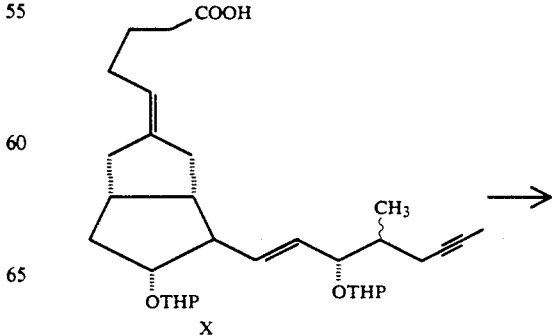
X

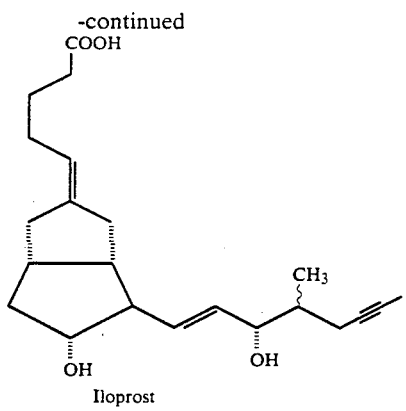

Iloprost

After regioselective blockage of the carbonyl group in Ia with formic acid ethyl ester in the presence of 2,2-dimethyl-1,3-diol and a catalytic amount of p-toluenesulfonic acid, Ib is reduced to the alcohol III with sodium borohydride in ethanol. Silyl ether formation (IV) and subsequent reduction with diisobutyl aluminum hydride in toluene at −70° C. yields the aldehyde V which is condensed to the α,β-unsaturated ketone VI with 3-methyl-2-oxohept-5-ynephosphonic acid dimethyl ester and sodium hydride. Reduction of the ketone VI to the alcohol VII, subsequent blocking group cleavage to the diol VIII and formation of the tetrahydropyranyl ether yields the ketone IX which is converted, after Wittig reaction with the ylene from 4-carboxybutyltriphenylphosphonium bromide and subsequent cleavage of blocking groups with aqueous acetic acid, into the carbayclin derivative iloprost.

The following practical embodiments serve for explaining the process of this invention.

EXAMPLE 1

10 g of 2,4-bisethoxycarbonylbicyclo[3.3.0]-octane-3,7-dione is dissolved in 40 ml of ethanol and diluted with 0.1-molar phosphate buffer pH 7 to a volume of 1,000 ml. Thereafter, 5 g of α-chymotrypsin from bovine pancreas (activity 1150 U/mg, Chemie Pharmazie Commerz, Hamburg) is added and the mixture shaken on a rotary shaker for 44 hours at 30° C. Then the reaction mixture is extracted three times with methyl isobutyl ketone, the extracts are combined and concentrated to dryness under vacuum. The remaining oily residue (9.4 g) is chromatographed for purification over a silica gel column by means of a solvent gradient of hexane/ethyl acetate. After evaporation of the main fraction, 6.68 g (89.7% of theory) of pure 2-ethoxycarbonylbicyclo[3.3.0]octane-3,7-dione is obtained as a pale, colorless oil which does not crystallize.

By comparing the CD spectrum with the spectrum of an identical comparison compound produced in some other way, it can be seen that the compound prepared in accordance with this invention exhibits enantiomer purity of above 98%.

EXAMPLE 2

One gram of 2,4-bismethoxycarbonylbicyclo[3.3.0]octane-3,7-dione is dissolved in 20 ml of methanol and combined with a solution of 2.5 g of α-chymotrypsin in 150 ml of 0.1-molar phosphate buffer pH 7. The solution is extracted with methyl isobutyl ketone after 22 hours of agitation at 28° C.; the extract is concentrated under vacuum, and the remaining residue is chromatographed over a silica gel column (gradient hexane/ethyl acetate), thus obtaining 610 mg of optically pure 2-methoxycarbonylbicyclo[3.3.0]octane-3,7-dione as an oily liquid.

EXAMPLE 3

3 g of 2,4-bisethoxycarbonyl-7,7-dimethoxybicyclo[3.3.0]octan-3-one is dissolved in 12 ml of ethanol and combined with 288 ml of 0.1-molar phosphate buffer pH 7. After adding 3 g of α-chymotrypsin, the mixture is shaken on a rotary shaker for 30 hours at 30° C. Subsequently, the reaction solution is freeze-dried and the remaining residue is eluted with methyl isobutyl ketone. The eluate is again brought to dryness and chromatographed over a silica gel column (gradient hexane/ethyl acetate). After evaporation of the main fraction, 1.64 g of optically pure 2-ethoxycarbonyl-7,7-dimethoxybicyclo[3.3.0]octan-3-one is obtained in the form of an oil that does not crystallize.

We claim:

1. A process for the production of optically active bicyclo[3.3.0]octanedione-carboxylic acid esters of Formula I

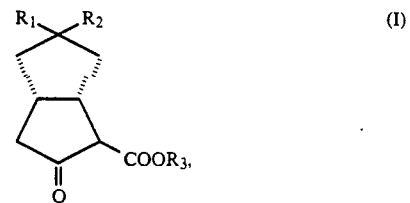

wherein
$R_1$ and $R_2$ jointly represent an oxygen atom, or
$R_1$ and $R_2$ individually represent the residue $OR_4$ where $R_4$ means methyl- or ethyl-, and
$R_3$ is a straight or branched-chain alkyl group of 1–3 carbons atoms,
comprising enantioselectively saponifying and decarboxylating with α-chymotrypsin an optically inactive, prochiral bicyclo[3.3.0]octanedionedicarboxylic acid diester of Formula II

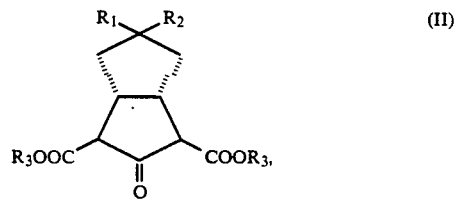

wherein $R_1$, $R_2$ and $R_3$ have the meanings set forth above, and recovering a compound of Formula I.

* * * * *